United States Patent
Saihata et al.

(10) Patent No.: US 6,291,712 B1
(45) Date of Patent: *Sep. 18, 2001

(54) PROCESS FOR PRODUCING SATURATED ALIPHATIC CARBOXYLIC ACID AMIDE

(75) Inventors: Shinya Saihata; Masaaki Katayama; Hitoshi Nakamura; Toshiyuki Aizawa, all of Oita (JP)

(73) Assignee: Showa Denko K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,802

(22) Filed: Nov. 26, 1997

Related U.S. Application Data (60) Provisional application No. 60/047,101, filed on May 19, 1997.

(51) Int. Cl.$^7$ .................................................. C07C 231/02
(52) U.S. Cl. ..................... 564/143; 564/134; 564/135; 564/137; 564/138
(58) Field of Search .................................... 524/134, 143, 524/135, 137, 138

(56) References Cited

FOREIGN PATENT DOCUMENTS

| 0 239 954 | 10/1987 | (EP) . |
| 935391 | * 8/1963 | (GB) . |
| WO94/15905 | 7/1994 | (WO) . |

OTHER PUBLICATIONS

Abstract XP002063876, "Preparation of carboxylic amide from ammonium salt and carboxylic acid—used as stabiliser of solvents and plasticisers, or base materials of e.g., dyes or pharmaceuticals", *Derwent Publcns. Ltd.,* Jun. 17, 1997.

Takahashi, K. et al., "The amidation of carboxylic acide with amine over hydrous zirconium (IV) oxide", *Bulletin of the Chemical Society of Japan,* XP–002063875, vol. 62, pp. 1333–1334, 1989.

* cited by examiner

*Primary Examiner*—Shailendra Kumar
(74) *Attorney, Agent, or Firm*—Sughrue, Mion, Zinn, Macpeak & Seas, PLLC (57) ABSTRACT

A process for producing a saturated aliphatic carboxylic acid amide, comprising reacting a saturated aliphatic carboxylic acid with ammonia to thereby obtain a saturated aliphatic ammonium carboxylate and subjecting the saturated aliphatic ammonium carboxylate to a dehydration reaction for obtaining a saturated aliphatic carboxylic acid amide, wherein the dehydration reaction of the saturated aliphatic ammonium carboxylate is conducted while supplying water to a reaction system in which the dehydration reaction is carried out. Preferably, water is continuously supplied to the reaction system so that the production of the saturated aliphatic carboxylic acid amide is carried out in a continuous manner and the amount of water present in a steady state ranges from 20 to 70 mol per 100 mol of a total of the saturated aliphatic carboxylic acid, the ammonia, the saturated aliphatic ammonium carboxylate, the saturated aliphatic carboxylic acid amide and the water. This process enables simplification of the production steps, ensures high operation efficiency, lowers production facility constructing and operating costs, reduces the amount of by-products and enables producing a high-purity carboxylic acid amide at a high selectivity, at a high yield and on an industrial scale.

11 Claims, 2 Drawing Sheets

FIG. 1

PROCESS FOR PRODUCING SATURATED ALIPHATIC CARBOXYLIC ACID AMIDE

This application is an application filed under 35 U.S.C. §111(a) claiming benefit pursuant to 35 U.S.C. §119(e)(1) of the filing date of the Provisional Application No. 60/047,101, filed May 19, 1997, pursuant to 35 U.S.C. §111(b).

FIELD OF THE INVENTION

The present invention relates to a process for producing a saturated aliphatic carboxylic acid amide (hereinafter often referred to simply as "carboxylic acid amide") which is widely used as solvents, solubilizing agents, plasticizer stabilizing agents, dyes, drugs and materials for use in organic syntheses. More particularly, the present invention is concerned with a process for effectively producing a highly purified carboxylic acid amide with the formation of by-products suppressed, in which a dehydration reaction of an ammonium salt obtained from corresponding saturated aliphatic carboxylic acid (hereinafter often referred to simply as "carboxylic acid") and ammonia is conducted while supplying water to the reaction system to thereby obtain a carboxylic acid amide.

Further, the present invention relates to a process in which part of water is separated and removed from a mixture of a saturated aliphatic ammonium carboxylate and water by distillation. More particularly, the present invention is concerned with a process for efficiently recovering a saturated aliphatic ammonium carboxylate by adding a saturated aliphatic carboxylic acid to a mixture of a saturated aliphatic ammonium carboxylate and water and thereafter conducting a distillation.

BACKGROUND OF THE INVENTION

It is known that the carboxylic acid amide can be produced by synthesizing an ammonium carboxylate salt from a carboxylic acid and ammonia and subjecting the salt to a dehydration reaction.

The carboxylic acid amide can be produced by a batch process or a continuous process. In an industrial process, conditions for separating and purifying the carboxylic acid amide as a product and conditions for removing and recycling by-products and unreacted raw materials are greatly influenced by, for example, the types and properties of desired carboxylic acid amide, individual starting materials and by-products. In particular, the cost and availability of raw materials, the final yield of desired product after separation and purification, the simplicity of entire production steps including a separation/purification system, the cost of production facility construction, the operation efficiency, the utility cost, etc. are extremely important factors, and an industrial process must be decided by collectively judging all of these. When the carboxylic acid amide is produced by, for example, a batch process, conventionally, the reaction temperature is set at 150 to 220° C. and the reaction time at 12 to 30 hr. and water formed as a by-product by the reaction is removed from the top of the reactor as a low boiling point fraction.

When the carboxylic acid amide is produced by this process, the conversion of the ammonium carboxylate can be 90% or higher. However, by-products such as nitrile compounds and carboxylic acid amide dimerization products are formed in relatively large amounts, so that the selectivity of carboxylic acid amide is as low as 90 to 95% and the final yield of carboxylic acid amide is also not satisfactory. Moreover, the production of carboxylic acid amide by the batch reaction prolongs the processing time and increases the formation of by-products, so that the above process cannot be regarded as an industrially advantageous process from a judgement of its productivity and economy.

For example, U.K. Patent No. 935,391 and Japanese Patent Laid-open Publication No. 57(1982)-38754 disclose a continuous process for producing a carboxylic acid amide, in which a carboxylic acid or an ammonium carboxylate is continuously fed into a reaction column through its top or its middle while ammonia is continuously fed into the reaction column through its lower part to thereby obtain a carboxylic acid amide.

In this process, with respect to reaction starting materials, ammonia is used in excess of the carboxylic acid. The excess ammonia is distilled out from the top of the reaction column together with water. For condensing the fraction from the top of the reaction column to thereby attain a recovery, a cooling medium of extremely low temperature must be used. Further, it is needed to install a separator for distilling water off recovered aqueous ammonia and install an absorption column for recovering ammonia gas obtained by this separation. Therefore, the above process cannot be regarded as a process which is satisfactory from the viewpoint of economy and operation efficiency.

In the process described in these published specifications, much of ammonia gas formed by a a decomposition reaction of ammonium carboxylate is distilled outside the system from the top of the reaction column. Therefore, the above process involves problems such that not only is the yield of carboxylic acid amide relative to the amount of ammonia added as a starting material unsatisfactory but also by-products such as nitrile compounds and carboxylic acid amide dimerization products (dimerized amide of carboxylic acid) are formed in relatively large amounts.

Therefore, there is a demand for the development of a process for producing a carboxylic acid amide, which enables producing a highly purified carboxylic acid amide at a high yield from a carboxylic acid and ammonia as raw materials.

In addition to the above processes, a process for producing a carboxylic acid amide has been proposed, in which the carboxylic acid amide is produced from an ammonium carboxylate in the presence of a dehydration catalyst. In this process, molybdenum oxide, an alkyltin catalyst, a mixture of silica gel and alumina or a titanium tetrachloride catalyst is used as the dehydration catalyst.

In this process, the dehydration reaction can be carried out at relatively low temperatures, so that not only can the formation of by-products such as nitrile compounds and carboxylic acid amide dimerization products be suppressed but also the reaction time can be shortened. However, when the carboxylic acid amide is produced with the use of the catalyst, it is apprehended that the catalyst be dissolved or otherwise contained in the obtained carboxylic acid amide and, hence, a step of separating or otherwise removing the catalyst from the carboxylic acid amide after the completion of the reactions becomes requisite. If costs of catalyst production and catalyst removal incurred by the use of the catalyst, etc. are taken into account, this process also cannot be regarded as a satisfactory process.

The applicant of the present patent application proposed in Japanese Patent Laid-open Publication No. 9(1997)-157233 a process for producing a carboxylic acid amide represented by the formula: $RCONH_2$ (wherein R represents a saturated alkyl group having 1 to 4 carbon atoms), comprising:

a first step comprising supplying, to a reactor consisting of a rectifying tower and a reaction vessel, a carboxylic acid represented by the formula RCOOH (wherein R is as defined above) and an ammonium salt thereof (provided that, in the total supply, the molar amount of the carboxylic acid is in the range of from 0.1 to 2.0 times that of the ammonium salt), which are fresh or recycled from the following second and third steps; conducting a dehydration reaction of the ammonium salt at 130 to 200° C.; and distilling mixture components consisting of formed water and the carboxylic acid and/or unreacted ammonium salt off the top of the rectifying tower to thereby obtain components containing the carboxylic acid amide from the reaction vessel;

a second step comprising distilling the components containing carboxylic acid amide obtained in the first step to thereby purify the carboxylic acid amide; and a third step comprising distilling water off the mixture components consisting of water and carboxylic acid and/or unreacted ammonium salt recovered in the first step.

This process enables producing a highly purified saturated lower alkyl carboxylic acid amide simply at a high yield with an industrial advantage, as compared with the above prior art processes. However, this process has room for improvement because by-products such as dicarboxylic acid amides and carboxylic acid salt of amidine are formed in a considerable amount in the dehydration reaction of the ammonium carboxylate for producing the carboxylic acid amide.

On the other hand, the obtained reaction mixtures containing carboxylic acid amide and water, including that obtained by the carboxylic acid amide producing process described in the above literature, generally also contain unreacted raw material ammonium carboxylate, etc. The reaction mixtures can be fractionated into low boiling point components such as ammonium carboxylate and water and high boiling point components such as carboxylic acid amide by a purification according to the customary distillation method. Thus, a carboxylic acid amide of relatively high purity can be obtained.

However, the lower aliphatic carboxylic acid amide has a relatively high boiling point and its thermal stability is poor at a temperature zone near the boiling point, so that, for example, the formation of impurities (by-products) is likely to occur in the purification stage. Main incidentally formed impurities include dicarboxylic acid amides which are amides resulting from dimerization of the carboxylic acid. The dicarboxylic acid amide and the carboxylic acid amide have approximately identical boiling points, so that these are obtained as high boiling point components. It is extremely difficult to purify the carboxylic acid amide by separating the same from the dicarboxylic acid amide with the use of customary distillation and purification means.

Further, it is known that this dicarboxylic acid amide is decomposed into a carboxylic acid and a nitrile compound when exposed to high temperature.

When it is intended to produce, for example, an N-vinyl carboxylic acid amide (one of useful vinyl monomers) by reacting a starting material of a carboxylic acid amide containing the above dicarboxylic acid amide as impurity with acetylene or the like at high temperatures, a decomposition reaction of the dicarboxylic acid amide simultaneously occurs in the production stage with the result that a carboxylic acid and a nitrile compound are formed. The formed carboxylic acid causes a deterioration of the reaction mixture containing the N-vinyl carboxylic acid amide, thereby inducing, for example, formation of polymers. As a result, troubles occur such as clogging of lines for production of the N-vinyl carboxylic acid amide, and the yield of the N-vinyl carboxylic acid amide drops. Therefore, it is not desirable to directly use the carboxylic acid amide containing the dicarboxylic acid amide as a starting material in the synthesis of the N-vinyl carboxylic acid amide.

The purification method combining the distillation method and the recrystallization method is generally known as providing means for obtaining a highly purified carboxylic acid amide not containing any dicarboxylic acid amide, which is suitably used as a starting material in the synthesis of, for example, an N-vinyl carboxylic acid amide. The use of the recrystallization method in combination with the distillation method provides An effective means for removing the dicarboxylic acid amide whose separation is difficult only by the distillation method. However, this recrystallization method generally employs an aqueous solution of alcohol in which the solubility of carboxylic acid amide is relatively high as a recrystallization solvent, so that, after the recrystallization, the carboxylic acid amide is present at a relatively high concentration in the mother liquor. Further, in this method, the yield of the carboxylic acid amide is so low that the mother liquor must be reprocessed for enhancing the yield. Still further, this method requires a drying step for removing the recrystallization solvent, which is disadvantageous from the viewpoint of cost.

For using the carboxylic acid amide containing dicarboxylic acid amide as a starting material in the synthesis of, for example, an N-vinyl carboxylic acid amide, it is required that some pretreatment be carried out to convert the dicarboxylic acid amide to components which are not detrimental to the production of an N-vinyl carboxylic acid amide, etc.

As mentioned above, the reaction mixture containing the carboxylic acid amide and water can be fractionated into high boiling point components composed mainly of the carboxylic acid amide and low boiling point components composed mainly of an ammonium carboxylate and water by the distillation method.

If recovered, the above ammonium carboxylate can be reutilized as a raw material for producing the carboxylic acid amide, and itself is useful as, for example, a dye buffer, an organic synthesis buffer, a raw material for drug or a raw material for organic synthesis.

It is important to remove water from the low boiling point components containing the ammonium carboxylate and water to thereby recover and reutilize the ammonium carboxylate from the viewpoint that the quantity of waste is reduced and that the carboxylic acid amide is produced at a high yield.

The removal of water from the low boiling point components (mixture) containing the ammonium carboxylate and water can be performed by the recrystallization method. The water separation according to the recrystallization method is performed by either cooling to below the crystallization temperature of the mixture or adding an to the ammonium carboxylate. In these recrystallization organic solvent such as an alcohol which is a poor solvent methods, the solubility of ammonium carboxylate in water is so high that the ammonium carboxylate is left in relatively high concentration in the residual liquid remaining after the recovery of ammonium carboxylate. For obtaining the ammonium carboxylate at a high yield, it is needed to further recover the ammonium carboxylate from the residual liquid. In the cooling crystallization method, when the water concentration (water content) is high, measures must be taken such that the crystallization temperature is set at an extremely low or that an organic solvent is added. When an organic solvent is used, it is additionally needed to implement a drying step for removing the organic solvent adhering to obtained crystals of ammonium carboxylate and a step for recycling the organic solvent. From the viewpoint of facility cost, productivity, etc. of these steps, the purification according to the cooling crystallization of ammonium carboxylate with the use of the organic solvent cannot be regarded as an effective purification method available in an industrial process.

On the other hand, in the method in which water is removed from the low boiling point components containing the ammonium carboxylate and water with the use of conventional distilling apparatus, the ammonium carboxylate is decomposed into a carboxylic acid and ammonia even at relatively low temperatures because its thermal stability is poor. The ammonia formed by the decomposition is distilled together with water off the top of the apparatus. When it is intended to recover the ammonia, an operation for further separating water from a fraction containing ammonia and water is needed. Thus, it is an nonefficient separating method and is not suitable to an industrial process. Therefore, there is a demand for the development of a simple economic technology for recovering the ammonium carboxylate from the low boiling point components containing the ammonium carboxylate and water.

As mentioned above, the carboxylic acid amide is produced by the dehydration reaction of the ammonium carboxylate. In the conventional method, side reactions occur and products of such side reactions (impurities) are concentrated and contained in the residue resulting from separation of the carboxylic acid amide from the reaction mixture. Although containing impurities much, this residue is composed mainly of the carboxylic acid amide. From the industrial point of view, it is desired to attain further recovery of the carboxylic acid amide from the above residue or attain effective utilization thereof, for example, recycling to the production stage.

Therefore, there is also a demand for the development of a process for producing a carboxylic acid amide, in which an effective utilization can be made of the residue resulting from recovery of the carboxylic acid amide from the carboxylic acid amide synthesizing reaction mixture and in which side reaction products that are detrimental to the quality of the carboxylic acid amide are not accumulated.

OBJECT OF THE INVENTION

The present invention has been made with a view toward resolving the above problems of the prior art. An object of the present invention is to provide a process for producing a carboxylic acid amide, which enables simplification of the production steps, ensures excellent operation efficiency, lowers production facility constructing and operating costs, reduces the amount of by-products and enables producing a highly purified carboxylic acid amide at a high selectivity, at a high yield and on an industrial scale.

Another object of the present invention is to provide a process for producing a carboxylic acid amide, which can attain an effective utilization of the residue resulting from recovery of the carboxylic acid amide and avoids accumulation, in the reaction system, of side reaction products that are detrimental to the production of the carboxylic acid amide.

An additional object of the present invention is to provide a process for purifying a carboxylic acid amide, in which a crude carboxylic acid amide containing a dicarboxylic acid amide is purified to thereby enable producing a highly purified carboxylic acid amide suitably usable as a raw material in the synthesis of an N-vinyl carboxylic acid amide simply, at a high yield and with an industrial advantage.

A further object of the present invention is to provide a process for efficiently producing a saturated aliphatic ammonium carboxylate by removing water from a mixture containing the ammonium carboxylate and water.

SUMMARY OF THE INVENTION

The process for producing a saturated aliphatic carboxylic acid amide according to the present invention comprises reacting a saturated aliphatic carboxylic acid with ammonia to thereby obtain a saturated aliphatic ammonium carboxylate and subjecting the saturated aliphatic ammonium carboxylate to a dehydration reaction for obtaining a saturated aliphatic carboxylic acid amide, wherein the dehydration reaction of the saturated aliphatic ammonium carboxylate is conducted while supplying water to a reaction system in which the dehydration reaction is being carried out.

In the present invention, preferably, water is supplied to the reaction system so that the production of the saturated aliphatic carboxylic acid amide is carried out in a continuous manner, and the amount of water present in a steady state ranges from 20 to 70 mol per 100 mol of a total of the saturated aliphatic carboxylic acid, the ammonia, the saturated aliphatic ammonium carboxylate, the saturated aliphatic carboxylic acid amide and the water.

The above process for producing a saturated aliphatic carboxylic acid amide according to the present invention preferably comprises:

[I] a first step comprising:

feeding to a reaction vessel, as raw materials, (a) the saturated aliphatic carboxylic acid, ammonia and water, and/or (b) the saturated aliphatic ammonium carboxylate and water, and conducting the dehydration reaction of the saturated aliphatic ammonium carboxylate in the presence of water to thereby form the saturated aliphatic carboxylic acid amide and water;

[II] a second step comprising distilling (preferably under reduced pressure) a reaction mixture obtained in the first step containing the saturated aliphatic carboxylic acid amide and water, in a first rectifying tower so that the reaction mixture is separated into low boiling point components containing the saturated aliphatic ammonium carboxylate and water and high boiling point components containing the saturated aliphatic carboxylic acid amide, thereby obtaining the saturated aliphatic carboxylic acid amide; and

[III] a third step comprising distilling off part of water from the low boiling point components obtained in the second step in a second rectifying tower to thereby obtain an aqueous solution of saturated aliphatic ammonium carboxylate and feeding the aqueous solution to the first step.

In the above processes of the present invention without exception, it is preferred that the dehydration reaction of the saturated aliphatic ammonium carboxylate be conducted at 130 to 250° C. under a pressure of 2 to 20 kgf/cm$^2$.

In the present invention, still preferably, the high boiling point components obtained in the second step, containing the saturated aliphatic carboxylic acid amide in high concentration, are further rectified to thereby separate the saturated aliphatic carboxylic acid amide from the high boiling point components to obtain a residue, and water is added to the residue to thereby hydrolyze side reaction products contained in the residue so that a mixture containing the saturated aliphatic carboxylic acid amide and the saturated aliphatic ammonium carboxylate is obtained, the above mixture recycled to the first step or the second step.

Also, it is preferred in the present invention that an alcohol of the formula: $R^2OH$ (wherein $R^2$ represents an alkyl group having 1 to 4 carbon atoms) be added to the high boiling point components obtained in the second step, containing the saturated aliphatic carboxylic acid amide in high concentration, to thereby carry out an alcoholysis of by-products contained in the high boiling point components, so that the saturated aliphatic carboxylic acid amide is obtained.

Further, it is preferred in the present invention that an alcohol of the formula: $R^2OH$ (wherein $R^2$ represents an alkyl group having 1 to 4 carbon atoms) be added to a distillate obtained by further rectifying the high boiling point components obtained in the second step, containing the saturated aliphatic carboxylic-acid amide in high concentration so as to separate the saturated aliphatic carboxylic acid amide, thereby carrying out an alcoholysis of by-products contained in the distillate with the result that the saturated aliphatic carboxylic acid amide is obtained.

In the present invention, the by-product is generally the saturated aliphatic dicarboxylic acid amide. The alcohol is preferably methanol.

Moreover, in the third step of the present invention, it is preferred that a saturated aliphatic carboxylic acid be added to the low boiling point components obtained in the second step, containing the saturated aliphatic ammonium carboxylate and water, and distilled in the presence of 0.1 to 10 mol of the saturated aliphatic carboxylic acid per mol of the saturated aliphatic ammonium carboxylate to thereby separate water.

In the present invention, preferably, the saturated aliphatic carboxylic acid is represented by the formula: $R^1COOH$ (wherein $R^1$ represents an alkyl group having 1 to 4 carbon atoms), the saturated aliphatic ammonium carboxylate is represented by the formula: $R^1COONH_4$ (wherein $R^1$ is as defined above) and the saturated aliphatic carboxylic acid amide is represented by the formula: $R^1CONH_2$ (wherein $R^1$ is as defined above). Still preferably, the saturated aliphatic carboxylic acid is acetic acid, the saturated aliphatic ammonium carboxylate is ammonium acetate and the saturated aliphatic carboxylic acid amide is acetamide.

The above process for producing a saturated aliphatic carboxylic acid amide according to the present invention enables simplification of the production steps, ensures excellent operation efficiency, lowers production facility constructing and operating costs, reduces the amount of by-products and enables producing a highly purified carboxylic acid amide at a high selectivity, at a high yield and on an industrial scale.

The present invention also provides a process for producing a carboxylic acid amide, which can attain an effective utilization of the residue resulting from recovery of the carboxylic acid amide and avoids accumulation, in the reaction system, of side reaction products that are detrimental to the production of the carboxylic acid amide.

Further, the present invention provides a process for purifying a carboxylic acid amide, in which a crude carboxylic acid amide containing a dicarboxylic acid amide is purified to thereby enable producing a highly purified carboxylic acid amide suitably usable as a raw material in the synthesis of an N-vinyl carboxylic acid amide simply, at a high yield and with an industrial advantage.

Still further, the present invention provides a process for efficiently producing a saturated aliphatic ammonium carboxylate by removing water from a mixture containing the ammonium carboxylate and water.

DETAILED DESCRIPTION OF THE INVENTION

The process for producing a saturated aliphatic carboxylic acid amide according to the present invention will be described in detail below.

Referring to the following formula, in the process for producing a saturated aliphatic carboxylic acid amide according to the present invention, which comprises reacting a saturated aliphatic carboxylic acid (e) with ammonia to thereby obtain a saturated aliphatic ammonium carboxylate (f) and subjecting the saturated aliphatic ammonium carboxylate to a dehydration reaction for obtaining a saturated aliphatic carboxylic acid amide (g), the dehydration reaction of the saturated aliphatic ammonium carboxylate (f) is conducted while supplying water to a reaction system in which the dehydration reaction is carried out.

$$R^1-\underset{\underset{O}{\|}}{C}-OH + NH_3 \longrightarrow$$
(e)

wherein $R^1$ represents an alkyl group, preferably, an alkyl group having 1 to 4 carbon atoms. Particularly preferred is methyl.

Conducting the above dehydration reaction while supplying water to the reaction system realizes hydrolyses of side reaction products such as dicarboxylic acid amides represented by the formula $(R^1CO)_2NH$ (wherein $R^1$ is as defined above) and carboxylic acid salts of amidine (h) of the formula:

wherein $R^1$ is as defined above. The above hydrolyses of the by-products convert the dicarboxylic acid amide as one of the by-products to corresponding carboxylic acid amide, carboxylic acid and the like and converts the amidine carboxylic acid salt to corresponding carboxylic acid amide, ammonium carboxylate and the like, so that a mixture composed mainly of the carboxylic acid amide and ammonium carboxylate (including water supplied for hydrolysis) can be obtained. Therefore, the amount of the above by-products whose adverse effect on the reaction system is apprehended can be reduced and accordingly the synthesis of the carboxylic acid amide can be performed at a high selectivity.

In this invention, water is supplied, preferably, continuously supplied to the reaction system so that the production of the saturated aliphatic carboxylic acid amide is carried out, and the amount of water present in a steady state ranges from 20 to 70 mol, preferably, 35 to 55 mol per 100 mol of a total of the saturated aliphatic carboxylic acid, the ammonia, the saturated aliphatic ammonium carboxylate, the saturated aliphatic carboxylic acid amide and the water.

It is preferred that the above dehydration reaction of the saturated aliphatic ammonium carboxylate be conducted at 130 to 250° C., especially, 160 to 200° C. under a pressure of 2 to 20 kgf/cm$^2$, especially, 4 to 10 kgf/cm$^2$. When the reaction temperature is lower than 130° C., the conversion of the ammonium salt is not satisfactorily high and the processing time is likely to prolong. On the other hand, when the reaction temperature is higher than 250° C., the formation of by-products is increased and the pressure of the reaction system becomes high to thereby necessitate an expensive pressure reaction vessel. This is disadvantageous from the viewpoint of cost. Although depending on reaction conditions such as reaction temperature, the reaction time generally ranges from 1 to 10 hr in terms of residence time.

The above saturated aliphatic carboxylic acid amide (carboxylic acid amide) is represented by the formula: $R^1CONH_2$ (wherein $R^1$ represents an alkyl group having 1 to 4 carbon atoms), which is, for example, acetamide, propionamice, iso-butyramide, n-butyramide, pivalamide iso-valeramide or n-valeramide, preferably, acetamide.

The carboxylic acid for use in the reaction or carboxylic acid for use in the production of the ammonium salt thereof is carboxylic acid corresponding to the above carboxylic acid amide, which is represented by the formula: $R^1COOH$ (wherein $R^1$ represents an alkyl group having 1 to 4 carbon atoms), which is, for example, acetic acid, propionic acid, iso-butyric acid, n-butyric acid, pivalic acid, iso-valeric acid or n-valeric acid.

The above process for producing the saturated aliphatic carboxylic acid amide (carboxylic acid amide) according to the present invention will be described in greater detail below with reference to the drawings.

Figure 1:
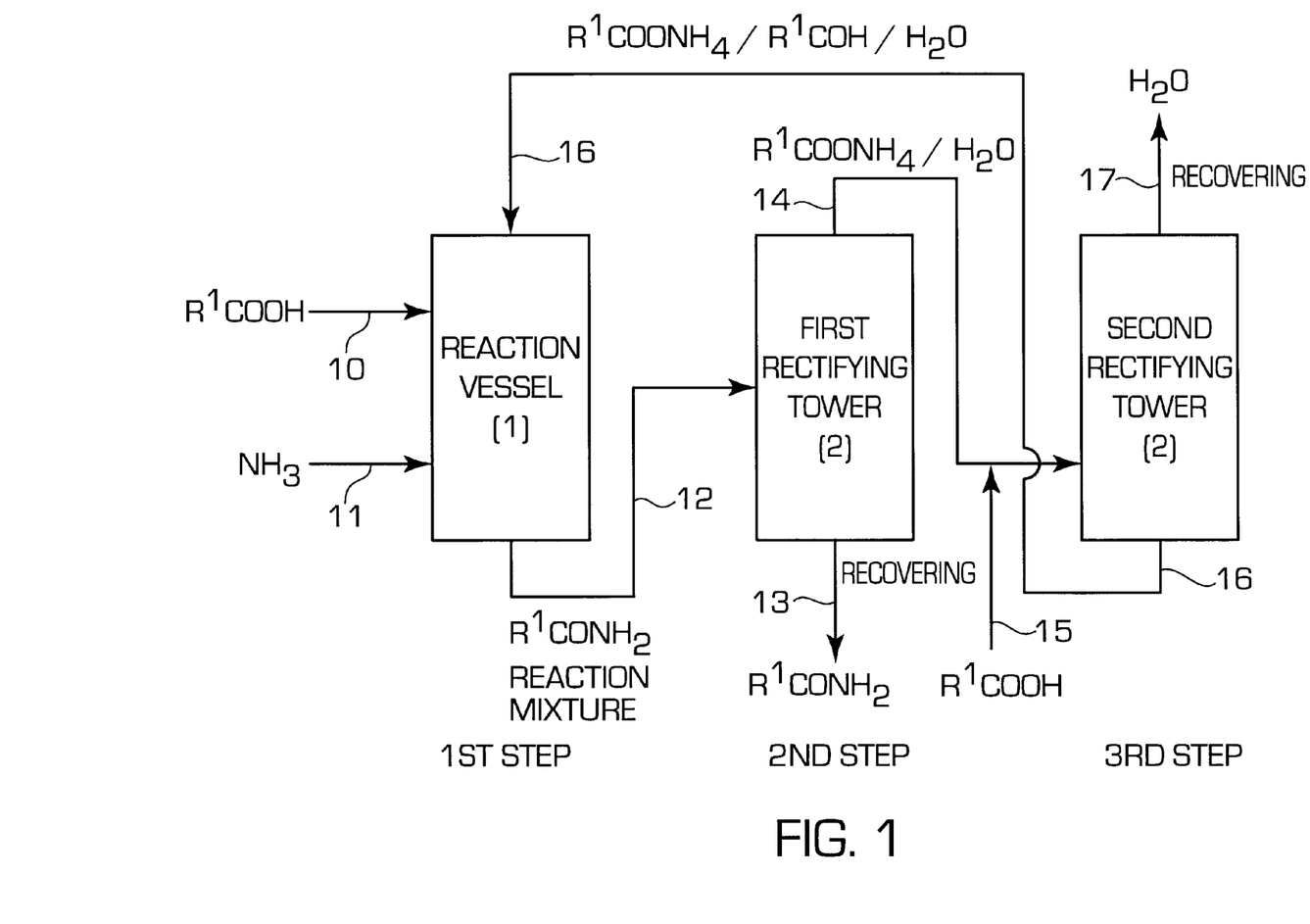
FIG. 1 is a schematic chart showing a preferred mode of the process for producing a saturated aliphatic carboxylic acid amide according to the present invention.

FIG. 1 is a schematic chart showing a preferred mode of the process for producing a saturated aliphatic carboxylic acid amide according to the present invention.

[First Step]

The process for producing a carboxylic acid amide as shown in FIG. 1 comprises first, second and third steps. In the first step [I], raw materials, specifically, (a) the saturated aliphatic carboxylic acid represented by the formula: $R^1COOH$ (wherein $R^1$ is as defined above), ammonia and water, and/or (b) the saturated aliphatic ammonium carboxylate represented by the formula: $R^1COONH_4$ (wherein $R^1$ is as defined above) and water, is fed into a reaction vessel (1) and the dehydration reaction of the saturated aliphatic ammonium carboxylate is conducted in the presence of water to thereby form the saturated aliphatic carboxylic acid amide and water.

In this first step, the dehydration reaction is conducted at 130 to 250° C., preferably, 160 to 200° C. Although depending on reaction conditions such as reaction temperature, the reaction time generally ranges from 1 to 10 hr in terms of residence time.

With respect to the molar ratio of raw materials fed into the reaction, it is desired that the carboxylic acid (including the carboxylic acid portion of the ammonium salt recycled from the second or third step) be used in an amount of 0.1 to 10 mol, especially, 0.5 to 2 mol and, still especially, 0.8 to 1.2 mol per mol of the ammonia (including the ammonia portion of the ammonium salt recycled from the second or third step).

The addition of the carboxylic acid in amounts larger than or smaller than the above range has little influence on the reaction performance, etc. However, the amount of recycled ammonia or carboxylic acid is increased, so that it is wasteful from the viewpoint of equipment and energy.

When the dehydration reaction is carried out under such conditions that the molar ratio of supplied carboxylic acid to supplied ammonia is smaller than 1, excess free ammonia component contained in the low boiling point fraction must be recovered in the below described distilling operation of the second step. In conducting the recovery, for example, an ammonia absorbing column is additionally needed for recovering ammonia. When the molar ratio of supplied carboxylic acid to supplied ammonia is close to 1, the apparatus to be introduced can be simple.

The method of supplying the raw materials to be fed into the reaction is not particularly limited. Like the carboxylic acid and ammonia in FIG. 1, each component may be separately directly fed into the reaction vessel. Alternatively, individual components may be mixed together and reacted in advance in a separate mixing tank (first reaction vessel) to thereby prepare a liquid mixture composed mainly of an ammonium carboxylate, followed by supply of the liquid mixture containing the ammonium carboxylate and water to a second reaction vessel in which the dehydration reaction is advanced in the presence of water. When the raw materials are directly fed into the reaction vessel (1) as shown in FIG. 1, in the reaction vessel (1), the ammonium salt of the carboxylic acid is immediately formed from the carboxylic acid and ammonia and the ammonium salt is dehydrated to thereby form the carboxylic acid amide.

Although the pressure under which the above dehydration reaction is conducted is not particularly limited, the above-mentioned pressure (2 to 20 kgf/cm$^2$) is generally employed. The reason is as follows. In the dehydration reaction, the operation is desirably conducted at high temperatures for efficiently advancing the dehydration reaction in the presence of supplied water or incidentally formed water without removing them as far as possible. Thus, the reaction is generally conducted under the above pressure. Although the pressure depends on the molar ratios of supplied carboxylic acid, ammonia and ammonium salt of the carboxylic acid used as raw materials, the operating temperature, etc., the above range of pressure is generally employed.

The reactor for use in the first step is not particularly limited as long as the reaction vessel thereof can resist the maximum of the pressure required for carrying out the above dehydration reaction, and there are no strict conditions on the structural form thereof.

[Second Step]

In the second step [II], the reaction mixture obtained in the above first step, containing the saturated aliphatic carboxylic acid amide and water, is distilled in a first rectifying tower (2) so that the reaction mixture is separated into low boiling point components containing the saturated aliphatic ammonium carboxylate and water and high boiling point components containing the saturated aliphatic carboxylic acid amide, thereby obtaining the saturated aliphatic carboxylic acid amide.

In the first rectifying tower (2) shown in FIG. 1, the mixture containing carboxylic acid amide obtained in the first step is supplied to the middle of the rectifying tower, and the highly purified carboxylic acid amide and low boiling point components are recovered from the bottom and the top of the rectifying tower, respectively.

The common distillation separation method is employed in the second step. The inside of the distilling apparatus may be held at any of reduced pressure, atmospheric pressure and superatmospheric pressure. Of these, reduced pressure is preferred from the viewpoint that the distillation temperature is lowered to thereby prevent the formation in large amount of by-products such as carboxylic acid amide dimerization products (dicarboxylic acid amides) and carboxylic acids and nitrile compounds both formed by pyrolysis of the dicarboxylic acid amide.

The rectification of the carboxylic acid amide in the second step is generally conducted in reduced pressure, preferably, a pressure of 1 to 400 Torr, still preferably, 10 to 100 Torr. The temperature distribution within the rectifying tower is determined by the set pressure (operating pressure), and the distillation operation is preferably conducted so that the temperature of the bottom of the rectifying tower becomes the boiling point of carboxylic acid amide at the operating pressure.

The composition of the carboxylic acid amide containing mixture obtained in the first step and supplied to the rectifying tower of the second step is mainly determined by the mixing ratio of raw materials fed in the first step and by the reaction conditions. Although the concentration of carboxylic acid amide is not particularly limited in the present invention, the use of a mixture of high carboxylic acid amide concentration is generally preferred from the viewpoint that the purity of the produced carboxylic acid amide is high and that the processing capacity is large irrespective of the same apparatus. Generally, the reaction mixture of 40 to 70% by weight in carboxylic acid amide concentration is supplied from the first step to the second step. Contained in the reaction mixture are not only the carboxylic acid amide but also water, further, ammonium carboxylates, carboxylic acid amide dimerization products (dicarboxylic acid amides) and amidine compounds (amidine carboxylic acid salts), and still further, depending on the mixing ratio of raw material fed in the first step, either of carboxylic acids and ammonia.

When an ammonia containing mixture is used as a raw material in the rectification of the second step, it is difficult to completely trap ammonia by means of a vapor condenser and noncondensed ammonia gas is generated. An ammonia absorbing step (not shown) is preferably implemented for absorbing this gas. Although the construction and mode of the ammonia gas absorbing step are not particularly limited, for effectively carrying out the present invention, it is preferred that a carboxylic acid like that being a raw material for producing the carboxylic acid amide, for example, acetic acid be used as an ammonia absorbing agent or ammonia trapping agent.

For example, a simple tower is used in the ammonia absorbing step. The carboxylic acid as an ammonia trapping agent is fed from the top of the tower while noncondensed gas composed mainly of ammonia is fed from a lower part of the tower so that a gas-liquid contact is made to thereby have ammonia, etc. absorbed. The thus recovered ammonia may be transferred to the first or third step for reutilization as a raw material. This operation enables reducing the amount of raw material required for obtaining a unit quantity of carboxylic acid amide (unit) to thereby attain a unit enhancement. Further, if the operation is conducted by vacuum system, the flow of ammonia gas into a vacuum pump is prevented.

Alternatively, the generation of noncondensed ammonia gas can be suppressed by using an effluent enriched with a carboxylic acid as a reflux fluid to the rectifying tower so that the carboxylic acid concentration of the vapor is increased.

There is no particular limitation with-respect to the position of the rectifying tower of the second step at which the mixture of the first step is to be supplied. However, it is requisite that a rectification zone exhibiting such a separation performance that the carboxylic acid amide can be satisfactorily separated from the effluent so as to avoid the flow of the carboxylic acid amide out of the top of the rectifying tower be disposed between the supply position and the top of the rectifying tower. It is also requisite that a rectification zone exhibiting such a separation performance that the carboxylic acid amide can be satisfactorily separated from low boiling point components such as carboxylic acids and ammonium salts thereof so as to avoid the flow of such low boiling point components in amounts exceeding tolerance levels out of the bottom of the rectifying tower be disposed between the supply position and the bottom of the rectifying tower.

The distilling apparatus used in the second step is not particularly limited, and no particular conditions are imposed on the structural form thereof. However, generally, use is made of distilling apparatus having a theoretical plate number of 1 to 100, preferably, 5 to 60 in the rectifying tower zone.

The rectifying tower can have any arbitrary structure. For example, use can be made of plate columns such as those including bubble cap trays, uniflux trays, flexi-trays, Nutter flow trays, ballast trays, porous plate trays, cascade trays, benturi trays, Kittel trays, recycling trays, chimney trays, jet trays, turbogrid trays, ripple trays, dual flow trays and baffle trays.

Further, use can be made of packed columns such as those including ring packing, saddle packing, spray pack, Pana pack, Goodroy packing, Stedman packing, McMahon packing, Sulzer packing, helix and vertical plate packing.

Although the reflux ratio of the second step is not particularly limited as long as it is set so that the outflow of carboxylic acid amide from the top of the rectifying tower is suppressed to the minimum extent possible and that the effluent from the top of the rectifying tower is a mixture composed mainly of ammonium salt and water, the reflux ratio is generally desired to range from 0.2 to 10.

The main components of the mixture recovered from the top of the rectifying tower are ammonium salt of the carboxylic acid which is used as a raw material in the reaction of the first step and water. The recovered mixture is fed to the third step.

The component withdrawn from the bottom of the rectifying tower is a highly purified carboxylic acid amide having 95 to 99.9% by weight of the carboxylic acid amide. Although this carboxylic acid amide as it is may be used as a product, the carboxylic acid amide after separation may be further purified to obtain a carboxylic acid amide of increased purity by any of the common purification methods such as the re-distillation purification method, extraction distillation purification method, crystallization purification method using various types of crystallizing devices, adsorption separation method and membrane separation method.

When the re-distillation purification method is executed, use is made of an apparatus in which a rectification zone exhibiting such a separation performance that the carboxylic acid amide can be satisfactorily separated from the high boiling point components so as to prevent high boiling point components from flowing out of the apparatus in amounts exceeding tolerance levels is disposed between the supply position and the top of the rectifying tower. This operation can also be performed by the simple distillation procedure, depending on the concentration of high boiling point components in the purification material and the concentration of high boiling point components tolerated by the desired carboxylic acid amide. Moreover, the highly purified carboxylic acid amide can be obtained by simultaneously separating low boiling point components and high boiling point components. In this operation, use is made of a purification apparatus equipped with a rectifying tower. Low boiling point components and high boiling point components are removed from an upper part and a lower part of the rectifying tower, respectively, and, simultaneously, the carboxylic acid amide is recovered from the middle or near a lower part of the rectifying tower. Thus, the desired component is obtained. In the rectifying tower of the purification apparatus, it is requisite that a rectification zone exhibiting such a separation performance that the carboxylic acid amide can be satisfactorily separated from the effluent so as to avoid the flow of the carboxylic acid amide out of the top of the rectifying tower be disposed between the supply position and the top of the rectifying tower. It is also requisite that a rectification zone exhibiting such a separation performance that the carboxylic acid amide can be satisfactorily separated from low boiling point components such as carboxylic acids and ammonium salts thereof so as to prevent such low boiling point components from being contained in the carboxylic acid amide in amounts exceeding tolerance levels be disposed between the supply position and the carboxylic acid amide recovering position. It is further requisite that a rectification zone exhibiting such a separation performance that the carboxylic acid amide can be satisfactorily separated from high boiling point components such as amidine compounds so as to prevent such high boiling point components from being contained in the carboxylic acid amide in amounts exceeding tolerance levels be disposed between the carboxylic acid amide recovering position and the bottom of the rectifying tower. The liquid residue resulting from execution of these purification operations can be recycled to the first step or third step, so that any conspicuous unit drop would not occur.

The method of fractionating the highly purified carboxylic acid amide from the above bottoms containing the carboxylic acid amide in high concentration will be described in detail below.

In the present invention, preferably, an alcohol of the formula: $R^2OH$ (wherein $R^2$ represents an alkyl group having 1 to 4 carbon atoms) is added to the high boiling point components obtained in the second step, containing the saturated aliphatic carboxylic acid amide in high concentration, to thereby carry out an alcoholysis of by-products contained in the high boiling point components, so that the saturated aliphatic carboxylic acid amide is obtained. Alternatively, preferably, an alcohol of the formula: $R^2OH$ (wherein $R^2$ represents an alkyl group having 1 to 4 carbon atoms) is added to a distillate obtained by further rectifying the high boiling point components obtained in the second step, containing the saturated aliphatic carboxylic acid amide in high concentration, so as to separate the saturated aliphatic carboxylic acid amide, thereby carrying out an alcoholysis of by-products contained in the distillate with the result that the saturated aliphatic carboxylic acid amide is obtained.

Illustratively, in the present invention, alcohol (b) is first added to a crude carboxylic acid amide containing dicarboxylic acid amide (a) to thereby prepare an alcohol solution of carboxylic acid amide. This solution is heated to thereby carry out such an alcoholysis of dicarboxylic acid amide (a) that the dicarboxylic acid amide (a) is decomposed into carboxylic acid amide (c) and carboxylic acid ester (d), as shown in the following formula. Thus, practical removal of the dicarboxylic acid amide can be attained.

wherein each of $R^1$ and $R^2$ independently represents an alkyl group having 1 to 4 carbon atoms.

This alcoholysis enables obtaining an alcohol solution of highly purified carboxylic acid amide (c) which does not contain dicarboxylic acid amides. Further purified carboxylic acid amide can be obtained by separating an alcohol and the carboxylic acid ester from this alcohol solution of highly purified carboxylic acid amide, according to necessity. The carboxylic acid ester (d) can be separated simultaneously with the alcoholysis or after the completion of the alcoholysis.

Lower alcohols are preferably used as the alcohol (b), and an appropriate one is selected from thereamong, taking into account the easiness in separating the obtained carboxylic acid amide (c) from the carboxylic acid ester (d) and in the purification thereof. Preferably, use is made of an alcohol represented by the formula $R^2OH$ (wherein $R^2$ represents an alkyl group having 1 to 4 carbon atoms), which is, for example, methanol, ethanol, n-propanol, isopropanol or n-butanol. Of these alcohols, methanol is especially preferred.

The above alcoholysis reaction is carried out at 50 to 200° C., preferably, 80 to 170° C. Conducting the alcoholysis reaction at temperatures lower than the above range retards the rate of alcoholysis of the dicarboxylic acid amide to thereby prolong the reaction time. On the other hand, raising the reaction temperature over the above range causes a thermal deterioration of the carboxylic acid amide to thereby lower the yield of carboxylic acid amide although the reaction rate is increased.

The reaction time is varied depending on the reaction temperature, the mixing molar ratio of dicarboxylic acid amide to alcohol, the concentration of dicarboxylic acid amide at the initiation of reaction, the mode of reaction, etc.

The reaction time may be set in conformity with conditions of these and the reaction time is not particularly limited. However, although the optimum reaction time is varied depending on the reaction temperature and mixing molar ratio of dicarboxylic acid amide to alcohol, the thermal deterioration of the carboxylic acid amide is generally proportional to the reaction time, so that it is preferred that the reaction be carried out within a short period of time.

The inside of the reactor may be held at any of reduced pressure, atmospheric pressure and superatmospheric pressure. Of these, atmospheric pressure is preferred. The reaction in reduced pressure causes a lowering of reaction performance and a prolongation of reaction time. The reaction under superatmospheric pressure requires a pressure resistant apparatus, which is disadvantageous from the viewpoint of cost.

Although the amount of alcohol added to the carboxylic acid amide is not particularly limited, it is preferred that the amount be determined in conformity with the amount of dicarboxylic acid amide contained in the carboxylic acid amide. Generally, the alcohol is preferably added in such an amount that the molar ratio of dicarboxylic acid amide to alcohol ranges from 1/1 to 1/1000, especially, from 1/10 to 1/100. An increase of the alcohol concentration lowers the boiling point of the system. Therefore, when it is intended to carry out the reaction at atmospheric pressure, the reaction temperature becomes so low that the reaction cannot be effectively carried out. The reaction temperature can be raised and the reaction time shortened by using a closed reactor and by carrying out the reaction under super-atmospheric pressure. However, this reaction requires a high pressure vessel. When the alcohol concentration is low, the alcoholysis (methanolysis) of dicarboxylic acid amide has a low reaction rate, also leading to disadvantageous conditions.

The reaction mode for carrying out the above alcoholysis reaction is not particularly limited. The reaction may be carried out under reflux conditions by setting the reaction temperature at the boiling point of the reaction fluid or may be operated with the vaporization suppressed at temperatures lower than the boiling point. The reaction may also be carried out at super-atmospheric pressure by using a closed reaction vessel.

Moreover, the employable reactor is not particularly limited, and there is no particular limitation on its structural form. When the reaction is carried out under reflux conditions, it is desirable to use a reaction vessel having a vapor condenser directly connected therewith. On the other hand, when the reaction is carried out at super-atmospheric pressure, it is desirable to use a high pressure reaction vessel which can resist the operating pressure.

The carboxylic acid amide is unstable in water and slowly decomposes by absorbing moisture from the air. Therefore, the reaction vessel and auxiliary facilities such as raw material tank and product tank are preferably held in atmosphere of, for example, nitrogen or dry air.

The separation of the carboxylic acid ester formed by the above alcoholysis can be performed simultaneously with the alcoholysis or after the completion of the alcoholysis. For example, low boiling point vapor containing the carboxylic acid ester may be generated by conducting the alcoholysis reaction at the boiling point of the reaction fluid. The boiling point of formed carboxylic acid ester is considerably lower than that of the carboxylic acid amide, so that the carboxylic acid ester is contained in the vapor in higher concentration. The carboxylic acid ester can be removed by expelling a condensate of the vapor outside the system. The separation of the carboxylic acid ester can be efficiently conducted by the use of a rectifying tower.

In the present invention, preferably, water is added to a residue (liquid residue) obtained by further rectifying the high boiling point components containing the saturated aliphatic carboxylic acid amide in high concentration according to any of the above various methods so as to separate the saturated aliphatic carboxylic acid amide, thereby carrying out a hydrolysis of side reaction products contained in the residue with the result that a mixture containing the saturated aliphatic carboxylic acid amide and saturated aliphatic ammonium carboxylate is obtained, this mixture being recycled to the first or second step.

This process will further be illustrated below.

In the production of the carboxylic acid amide through the dehydration reaction of the ammonium carboxylate, main reaction by-products are the above dicarboxylic acid amide represented by the general formula $(R^1CO)_2NH$ (wherein $R^1$ is as defined above) and carboxylic acid salt of amidine represented by the formula $R^1C(NH)(NH_2)$ (wherein $R^1$ is as defined above). These reaction by-products are generally contained in a concentrated state in the residue (liquid residue) resulting from a separation of the carboxylic acid amide from the synthetic reaction fluid by the distillation, crystallization or other method.

In the present invention, the above hydrolytic reaction by adding water to the residue converts the dicarboxylic acid amide to corresponding carboxylic acid amide, carboxylic acid and the like and converts the amidine carboxylic acid salt to corresponding carboxylic acid amide, ammonium carboxylate and the like, so that a mixture composed mainly of the carboxylic acid amide and ammonium carboxylate (including water supplied for hydrolysis) can be obtained.

The thus obtained mixture composed mainly of the carboxylic acid amide and ammonium carboxylate can be recycled to the first or second step for use as a part of raw material in the production of the carboxylic acid amide from the ammonium carboxylate or for reutilization (recycle) in the rectifying tower of the second step. Thus, high efficiency is ensured.

When a selective hydrolysis of side reaction products is conducted by adding water to the residue or by adding the residue to water, it is preferred that conditions under which a hydrolysis of the carboxylic acid amide as a principal component can be suppressed to the minimum extent possible be adopted. It is believed that the dicarboxylic acid amide and amidine carboxylic acid salt are more readily hydrolyzed than the carboxylic acid amide. Although the presence of an acid or base catalyst can increase the rate of hydrolysis of reaction by-products, the carboxylic acid amide also becomes readily hydrolyzed, thereby unfavorably lowering the selectivity.

The amount of water added to the residue is generally adjusted so that the water accounts for 1 to 50% by weight based on the weight of the whole of the residue plus added water, although depending on the amount of reaction by-products contained in the residue. When the amount of water exceeds the above range, the hydrolysis of the carboxylic acid amide is advanced so that the selectivity is lowered. On the other hand, when it is smaller than the above range, the hydrolysis of reaction by-products is retarded to thereby prolong the reaction time to an extent of inefficiency.

This hydrolysis reaction is generally conducted at 50 to 300° C., preferably, 100 to 200° C. at atmospheric pressure. This hydrolysis reaction may be conducted under super-atmospheric pressure. The residue having been subjected to the selective hydrolysis reaction of side reaction products may be individually subjected to a separation of the carboxylic acid amide or may be first mixed with the synthetic reaction fluid of carboxylic acid amide and then subjected to a separation of the carboxylic acid amide.

The above process in which water is added to the residue (liquid residue) resulting from fractionation of the saturated aliphatic carboxylic acid amide to thereby carry out a hydrolysis of side reaction products contained in the residue with the result that a mixture containing the saturated aliphatic carboxylic acid amide and saturated aliphatic ammonium carboxylate is obtained can be effectively applied to not only the above residue resulting from fractionation of the highly purified saturated aliphatic carboxylic acid amide, obtained in the second step of the present invention, but also the residue resulting from fractionation of the saturated aliphatic carboxylic acid amide, obtained by the conventional method.

[Third Step]

In the third step [III] shown in FIG. 1, part of water is distilled off from the low boiling point components obtained in the second step in a second rectifying tower (3) to thereby obtain an aqueous solution of saturated aliphatic ammonium carboxylate, and this aqueous solution is recycled to the reactor (1) of the first step.

Illustratively, this third step comprises distilling off part of water from the low boiling point components (mixture) recovered from the top of the first rectifying tower in the second step, containing the ammonium carboxylate and water as principal components, to thereby obtain an aqueous solution of ammonium carboxylate as a principal component and feeding the obtained aqueous solution of ammonium carboxylate (recovered component) to the first step.

The rectifying operation is performed according to the same common distillation separation method as in the second step. The inside of the distilling apparatus may be held at any of reduced pressure, atmospheric pressure and superatmospheric pressure. Of these, reduced pressure is preferred. Although the distillation temperature is not particularly limited, distillation at high temperatures accelerates the decomposition reaction of ammonium carboxylates to thereby invite the flow of ammonia together with water from an upper part of the distilling apparatus. Thus, an aqueous ammonia separating step for distilling ammonia from the fraction is additionally needed. Therefore, it is generally preferred that the distillation be conducted at 150° C. or below, especially, 120° C. or below as measured at the lowest part inside the apparatus (distillation column bottom temperature).

It is preferred that the rectifying operation be performed in reduced pressure, especially, reduced pressure of 1 to 600 Torr, still especially, 10 to 400 Torr and yet still especially 50 to 300 Torr. The temperature distribution within the rectifying tower is determined by the operating pressure.

The composition of the fraction recovered from the top of the first rectifying tower of the second step and supplied as a charge material to the third step is mainly determined by the mixing ratio of raw materials fed in the first step and by the reaction conditions.

The fraction recovered from the top of the first rectifying tower is generally a liquid mixture containing not only ammonium carboxylate and water but also carboxylic acids or ammonia.

Although this liquid mixture (charge material for rectification in the third step) may be directly fed into the distilling apparatus (3) to thereby conduct the distilling operation, it is preferred that a carboxylic acid or ammonia be fed into the liquid mixture to thereby attain such a adjustment that the carboxylic acid is present slightly in excess in the liquid mixture to be supplied to the third step with none of free ammonia present therein, prior to conducting the distilling operation of the third step. That is, it is preferred that such an adjustment that the molar ratio of ammonium carboxylate to carboxylic acid in the liquid mixture ranges from 1/0.1 to 1/10, especially, from 1/0.25 to 1/2 be made prior to supplying the liquid mixture to the third step.

When the carboxylic acid is added in excess of the ammonium salt thereof, the decomposition reaction of the ammonium salt is suppressed. Further, even if ammonia gas is generated by the decomposition reaction of the ammonium carboxylate, the carboxylic acid exerts an action as trapping agent, so that the flow of ammonia from an upper part of the distilling apparatus (3) of the third step can be suppressed. Moreover, the water content of the ammonium carboxylate component recovered from a lower part of this apparatus and recycled to the first step can be reduced and the theoretical plate number of the distillation column used in the third step can be decreased thereby.

However, when the carboxylic acid is added to the purification charge material of the third step in excess of the above ratio, the carboxylic acid is distilled out from an upper part of the apparatus. Thus, a step for separating the carboxylic acid and water is additionally needed, which is disadvantageous from the viewpoint of cost.

The distilling apparatus used in the third step is not particularly limited, and no-particular conditions are imposed on the structural form thereof. However, generally, use is made of distilling apparatus having a theoretical plate number of 1 to 100, preferably, 5 to 60 in the rectifying tower zone. The rectifying tower can have any arbitrary structure. For example, use can be made of the above-mentioned plate columns and packed-columns.

Although the charge material supply position is not particularly limited, it is desired that a rectification zone exhibiting such a separation performance that the carboxylic acid or ammonia is not distilled out of the top of the rectifying tower in an amount exceeding tolerance level be disposed between the charge material supply position and the top of the rectifying tower and that a rectification zone exhibiting such a separation performance that water is not discharged from the bottom of the rectifying tower in an amount exceeding tolerance level be disposed between the charge material supply position and the bottom of the rectifying tower.

The rectification conditions are preferably so set that the flow of ammonium carboxylate, carboxylic acid and ammonia from the top of the rectifying tower can be suppressed and that, as completely as possible, only water is distilled off the tower top. It is generally desired that the reflux ratio range from 0.2 to 10.

The recovered material from the tower bottom is a mixture comprising ammonium carboxylate and water as main component, and optionally carboxylic acid.

The mixture is fed to the first step to reutilize thereof.

Ammonia may be added in an amount equimolar to that of the carboxylic acid contained in the mixture recovered from the tower bottom (recovered material) so that the carboxylic acid reacts with ammonia to form ammonium carboxylate, thereby increasing the purity of ammonium carboxylate.

As apparent from the foregoing description, the process for producing a carboxylic acid amide according to the present invention is characterized in that the dehydration reaction of the ammonium carboxylate obtained from the carboxylic acid and ammonia is advanced in the presence of a large amount of water which is contained in the components recycled from the second step and/or third step and formed in accordance with the progress of the dehydration reaction. Further, it is characterized in that the dehydration reaction is advanced under such conditions that the undesired formation of carboxylic acid amide dimerization products, nitrile compounds and amidine compounds is suppressed. As a result, production of the carboxylic acid amide with a high selectivity has been realized.

In the prior art method, water incidentally formed during the production of the carboxylic acid amide is recovered together with the carboxylic acid or ammonia. By contrast, in the present invention, water is fractionated as a liquid mixture composed mainly of water and the ammonium carboxylate; separation of part of water from this liquid mixture is performed by carrying out distilling operation at relatively low temperatures such that the rate of decomposition of ammonium carboxylate is low; and the separation is conducted in the presence of the carboxylic acid with the result that efficient removal of water with the use of simple apparatus has been realized.

Moreover, the dicarboxylic acid amide incidentally produced during the production of the carboxylic acid amide has a boiling point which is close to that of the carboxylic acid amide and the thermal stability of the carboxylic acid amide is poor around the boiling point of the dicarboxylic acid amide. Thus, in the prior art, it has been difficult to separate them by a simple method, as mentioned hereinbefore. However, in the present invention, the alcohol is added to the crude carboxylic acid amide containing the dicarboxylic acid amide and heated to thereby perform the alcoholysis of the dicarboxylic acid amide into the carboxylic acid amide and carboxylic acid ester. Thus, substantially complete removal of the dicarboxylic acid amide while preventing deterioration of the carboxylic acid amide is attained by a simple method such as distillation utilizing the significant boiling point difference between the carboxylic acid amide and the carboxylic acid ester. Consequently, obtaining the highly purified carboxylic acid amide has been enabled.

EFFECT OF THE INVENTION

In the process for producing a carboxylic acid amide according to the present invention, the dehydration. reaction of the ammonium carboxylate obtained from the carboxylic acid and ammonia is advanced under a supply of water to thereby suppress the formation of by-products such as carboxylic acid amide dimerization products, nitrile compounds and amidine compounds to an extremely low level. As a result, production of the carboxylic acid amide with a high selectivity has been realized.

In the third step thereof, the separation of water from the ammonium carboxylate is performed in the presence of free carboxylic acid to thereby efficiently remove water by means of simple apparatus with the result that fractionation of the ammonium carboxylate has been realized.

Therefore, the present invention has enabled simplification of the production steps, has ensured excellent operation efficiency, has lowered production facility constructing and operating costs, has reduced the amount of by-products and has enabled producing the highly purified carboxylic acid amide at a high selectivity, at a high yield and on an industrial scale.

Further, the present invention has established a process for producing the carboxylic acid amide, which can attain an effective utilization of the residue resulting from recovery of the carboxylic acid amide and avoids accumulation, in the reaction system, of side reaction products that are detrimental to the production of the carboxylic acid amide.

Still further, the present invention has established a process for purifying the carboxylic acid amide, in which the crude carboxylic acid amide containing the dicarboxylic acid amide is purified to thereby enable producing the highly purified carboxylic acid amide which is suitably usable as a raw material in the synthesis of an N-vinyl carboxylic acid amide, simply, at a high yield and with an industrial advantage.

EXAMPLE

The present invention will now be illustrated in greater detail with reference to the following Examples, which in no way limit the scope of the invention.

Example A1

[First Step]

Acetic acid, ammonia and the 20:15:10 (in molar ratio) mixture of ammonium acetate, acetic acid and water recycled from the third step were continuously supplied in respective rates of 61.2, 24.5 and 73.3 kg/hr to a reaction vessel of 1 m$^3$ in volume equipped with an agitator, which reaction vessel had its temperature and pressure maintained at 170° C. and 5 kgf/cm$^2$, respectively. Simultaneously, a mixture (liquid) containing acetamide in a concentration of 54% by weight was continuously withdrawn at a rate of 159 kg/hr.

The amount of steady-state water in the reaction vessel was 47 mol per 100 mol of the total of acetic acid, ammonia, ammonium acetate, acetamide and water. In the withdrawn mixture, the ammonium acetate conversion was 72% and the acetamide selectivity was 99%.

[Second Step]

The mixture (liquid) containing acetamide in a concentration of 54% by weight, withdrawn from the first step, was continuously supplied to the middle of a rectifying tower of 22 in theoretical plate number packed with McMahon packing at a rate of 159 kg/hr. The distilling operation was conducted at a pressure of 50 Torr and at a reflux ratio of 2. The temperature of the bottom of the distillation column was 142° C.

Concentrate was recovered from the tower bottom at a rate of 85.0 kg/hr. The acetamide concentration of the concentrate was 99% by weight. A mixture of ammonium acetate and water was recovered from the tower top at a rate of 74.1 kg/hr.

[Third Step]

Acetic acid was added to the mixture of ammonium acetate and water being the low boiling point components of the second step, obtained as the rectifying tower overhead, so that the molar ratio of ammonium acetate to acetic acid was 1:0.75. The resultant mixture was continuously supplied to a lower plate of a rectifying tower of 10 in theoretical plate number packed with McMahon packing at a rate of 99.3 kg/hr. The distilling operation was conducted at a pressure of 200 Torr and at a reflux ratio of 2. The temperature of the bottom of the distillation column was 100° C.

Consequently, a 1:0.75:0.5 (in molar ratio) mixture of ammonium acetate, acetic acid and water having an ammonium acetate concentration of 59% by weight was recovered from the tower bottom at a rate of 73.4 kg/hr and an overhead of 99.5% by weight in water concentration was recovered from the tower top at a rate of 25.9 kg/hr. The bottoms were reutilized as the raw material in the reaction of the first step.

Comparative Example A1

1000 kg of ammonium acetate was charged into a reaction vessel of 2 m$^3$ in internal volume equipped with an agitator and also equipped with a rectifying tower of 14 in theoretical plate number packed with McMahon packing and slowly heated. The reaction was carried out while recovering water formed in accordance with the advance of dehydration reaction from an upper part of the apparatus. The internal temperature of the reaction vessel was raised to, finally, about 180° C. The acetamide concentration of recovered reaction fluid was about 60% by weight, and the ammonium acetate conversion and acetamide selectivity were 95% and 94%, respectively.

Example B1

[Method of Synthesizing Acetamide]

Acetic acid and ammonia were continuously supplied in respective rates of 60 and 17 kg/hr to a reaction vessel of 0.6 m$^3$ in volume equipped with an agitator, which reaction vessel had its temperature and pressure maintained at 170° C. and 6 kgf/cm$^2$, respectively. Simultaneously, a reaction mixture (liquid) containing acetamide in a concentration of about 54% by weight was continuously withdrawn from the reaction vessel at a rate of 77 kg/hr. The reaction was carried out at a residence time of 6 hr, and the ammonium acetate conversion and acetamide selectivity were 72% and 99%, respectively.

The composition of the reaction mixture is given in Table B1.

TABLE B1

| Composition | wt. % |
| --- | --- |
| acetamide | 53.7 |
| water | 18.7 |
| ammonium acetate | 27.1 |
| acetic acid salt of acetamidine | 0.4 |

[Method of Separating Acetamide]

The reaction mixture (liquid) containing acetamide in a concentration of about 54% by weight was continuously supplied to the middle of a rectifying tower of 22 in theoretical plate number packed with McMahon packing at a rate of 77 kg/hr. The distilling operation was conducted at a pressure of 50 mmHg and at a reflux ratio of 2. The temperature of the bottom of the distillation column was 143° C.

Concentrate was recovered from the tower bottom at a rate of 42 kg/hr. The acetamide concentration of the concentrate was 99% by weight. A mixture of ammonium acetate and water was recovered from the tower top at a rate of 35 kg/hr.

The resultant concentrate was subjected to a simple distillation performed at 110° C. and at a pressure of 10 mmHg while continuously supplying the same at a rate of 42 kg/hr to thereby separate acetamide component. Thus, highly purified acetamide (99.7% by weight in purity) was obtained. The residue was recovered from a lower part of the apparatus at a rate of 4 kg/hr. The composition of the residue is as specified in the following Table B2.

TABLE B2

| Composition | wt. % |
| --- | --- |
| acetamide | 97.7 |
| diacetamide | 0.3 |
| acetic acid salt of acetamidine | 2.0 |

[Method of Hydrolyzing Residue]

The residue with the composition of Table B2 and water were continuously added to a pressure resistant reaction vessel at rates of 3 and 1 kg/hr, respectively and reacted at 170° C., an operating pressure of 5.5 kgf/cm$^2$ and a residence time of 6 hr. Simultaneously, the reaction fluid was withdrawn therefrom at a rate of 4 kg/hr.

The composition of recovered reaction product is specified in the following Table B3. After the completion of the reaction, the diacetamide conversion and conversion of acetic acid salt of acetamidine were 95 and 80%, respectively.

TABLE B3

| Composition | wt. % |
| --- | --- |
| acetamide | 59.6 |
| diacetamide | 0.01 |
| acetic acid salt of acetamidine | 0.3 |
| water | 20.7 |
| ammonium acetate | 19.4 |

The obtained reaction fluid was recycled to the acetamide purifying stage (second step) and used as part of the feed material.

Example B2

A carboxylic acid amide was produced in the same manner as in Example B1, except that the reaction conditions were as follows.

Specifically, acetic acid and ammonia were continuously supplied in respective rates of 60 and 17 kg/hr to a pressure resistant reaction vessel of 0.6 m$^3$ in volume and, further, the residue with the composition of Table B2, obtained in the same manner as in Example B1, was continuously fed thereto at a rate of 3 kg/hr. The reaction fluid was continuously withdrawn from the reaction vessel at a rate of 80 kg/hr. The reaction was carried out at 170° C. and at a residence time of 6 hr with the reaction pressure set at 5.5 kgf/cm$^2$.

Thereafter, the production of the carboxylic acid amide was performed in the same manner as in Example B1.

The composition of obtained reaction product is specified in the following Table B4.

TABLE B4

| Composition | wt. % |
| --- | --- |
| acetamide | 60.7 |
| diacetamide | 0.01 |
| acetic acid salt of acetamidine | 0.4 |
| water | 18.3 |
| ammonium acetate | 20.6 |

Comparative Example B1

A carboxylic acid amide was produced in the same manner as in Example B2, except that the reaction conditions were as follows.

Specifically, acetic acid and ammonia were continuously fed in respective rates of 60 and 17 kg/hr to the same pressure resistant reaction vessel as used in Example B2. The reaction fluid was continuously withdrawn from the reaction vessel at a rate of 77 kg/hr. The reaction was carried out at 170° C. and at a residence time of 6 hr with the reaction pressure set at 6 kgf/cm$^2$.

Thereafter, the production of the carboxylic acid amide was performed in the same manner as in Example B2.

The composition of obtained reaction product is specified in the following Table B5.

TABLE B5

| Composition | wt. % |
| --- | --- |
| acetamide | 54.1 |
| diacetamide | 0.01 |
| acetic acid salt of acetamidine | 0.4 |
| water | 18.3 |
| ammonium acetate | 27.2 |

The ratios of diacetamide and acetic acid salt of acetamidine to acetamide were the same as in Example B2 in which the residue was added as part of the charge material.

Reference Example B1
[Method of Synthesizing Acetamide]

Acetic acid and ammonia were continuously supplied in respective rates of 192 and 34 kg/hr to a reaction vessel of 2 m³ in volume equipped with an agitator and also equipped with a rectifying tower of 14 in theoretical plate number packed with McMahon packing. The operation was carried out at a reaction vessel internal temperature of 170° C., a reflux ratio of 2 and a residence time of 6 hr.

A reaction fluid of 60% by weight in acetamide concentration was recovered from the reaction vessel part at a rate of 186 kg/hr, and a 1:0.06 (in molar ratio) mixture of water and acetic acid was recovered from the top of the distillation column at a rate of 40 kg/hr. The conversion of ammonium acetate obtained from acetic acid and ammonia was 95% and the acetamide selectivity was 95%.

[Method of Separating Acetamide]

The reaction mixture (liquid) containing acetamide in a concentration of 60% by weight was continuously supplied to the middle of a rectifying tower of 22 in theoretical plate number packed with McMahon packing at a rate of 186 kg/hr. The distilling operation was conducted at a pressure of 50 mmHg and at a reflux ratio of 2. The temperature of the bottom of the distillation column was 143° C. Concentrate was recovered from the tower bottom at a rate of 116 kg/hr. The acetamide concentration of the concentrate was 97% by weight.

The resultant concentrate was subjected to a simple distillation performed at 110° C. and at a pressure of 10 mmHg while continuously supplying the same at a rate of 116 kg/hr to thereby separate acetamide component. Thus, highly purified acetamide (99.5% by weight in purity) was obtained. The residue was recovered from a lower part of the apparatus at a rate of 12 kg/hr. The composition of the residue is as specified in the following Table B6.

TABLE B6

| Composition | wt. % |
| --- | --- |
| acetamide | 92.2 |
| diacetamide | 0.3 |
| acetic acid salt of acetamidine | 7.5 |

[Method of Hydrolyzing Residue]

The residue with the composition of Table B6 and water were continuously added to a pressure resistant reaction vessel at rates of 12 and 4 kg/hr, respectively and, simultaneously, the reaction fluid was withdrawn therefrom at a rate of 16 kg/hr. The reaction was carried out at 170° C., an operating pressure of 5.5 kgf/cm² and a residence time of 6 hr. The composition of recovered reaction product is specified in the following Table B7. After the completion of the reaction, the diacetamide conversion and conversion of acetic acid salt of acetamidine were 96 and 91%, respectively.

TABLE B7

| Composition | wt. % |
| --- | --- |
| acetamide | 59.6 |
| diacetamide | 0.01 |
| acetic acid salt of acetamidine | 0.5 |
| water | 20.7 |
| ammonium acetate | 19.4 |

The obtained reaction fluid was recycled to the acetamide synthesizing stage and used as part of the raw material for acetamide.

Example C1

A mixture comprising 99.5% by weight of acetamide and 0.3% by weight of diacetamide together with water, acetic acid, etc. was continuously fed at a rate of 90 kg/hr into a reaction vessel of 4 m³ in volume equipped with a vapor condenser, and also methanol was continuously fed thereinto at a rate of 10 kg/hr. The operation was carried out at a reaction vessel temperature of 115° C. and at a reaction fluid volume of 2 m³. The reaction fluid was continuously withdrawn at a rate of 100 kg/hr. The rise of a vapor composed mainly of methanol from an upper part of the reaction vessel was recognized, which was condensed by means of a vapor condenser and recycled to the reaction vessel. The diacetamide conversion was 92%.

Example C2

A mixture comprising 99.5% by weight of acetamide and 0.3% by weight of diacetamide together with water, acetic acid, etc. was continuously fed at a rate of 95 kg/hr into a reaction vessel of 4 m³ in volume, and also methanol was continuously fed thereinto at a rate of 5 kg/hr. The operation was carried out at a reaction vessel temperature of 120° C. and at a reaction fluid volume of 3 m³. The reaction fluid was continuously withdrawn at a rate of 100 kg/hr. The diacetamide conversion was 90%.

Example C3

Low boiling point components were distilled from the reaction fluid obtained in Example C1, thereby obtaining acetamide product (highly purified acetamide) of at least 99.9% by weight in purity having a diacetamide concentration of less than 0.03% by weight at a rate of 89 kg/hr.

Example D1

Acetic acid was added to an aqueous ammonium acetate solution comprising ammonium acetate and water in a molar ratio of 1:4 in an amount of 0.7 time the mole of ammonium acetate. The resultant mixture was continuously supplied to a lower plate of a rectifying tower of 10 in theoretical plate number packed with McMahon packing at a rate of 100 kg/hr. The distilling operation was conducted at a pressure of 200 Torr and at a reflux ratio of 2. The temperature of the bottom of the distillation column was 100° C.

Consequently, a 1:0.7:0.5 (in molar ratio) mixture of ammonium acetate, acetic acid and water was recovered from the tower bottom at a rate of 67 kg/hr and an overhead of 99.5% by weight in water concentration was recovered from the tower top at a rate of 33 kg/hr.

Example D2

Acetic acid was added to an aqueous ammonium acetate solution comprising ammonium acetate, acetic acid and water in a molar ratio of 1:0.2:5, thereby preparing an aqueous solution comprising ammonium acetate, acetic acid and water in a molar ratio of 1:1:5. The resultant aqueous solution was continuously supplied to a lower plate of a rectifying tower of 10 in theoretical plate number packed with McMahon packing at a rate of 100 kg/hr. The distilling operation was conducted at a pressure of 200 Torr and at a reflux ratio of 2. The temperature of the bottom of the distillation column was 100° C.

Consequently, a 1:1:0.2 (in molar ratio) mixture of ammonium acetate, acetic acid and water was recovered from the tower bottom at a rate of 61 kg/hr and an overhead of 98.0% by weight in water concentration was recovered from the tower top at a rate of 39 kg/hr.

Example D3

Acetic acid was added to an aqueous ammonium acetate solution comprising ammonium acetate and water in a molar ratio of 1:4 in an amount of 0.7 time the mole of ammonium acetate. The resultant mixture was continuously supplied to a lower plate of a rectifying tower of 10 in theoretical plate number packed with McMahon packing at a rate of 100 kg/hr. The distilling operation was conducted at a pressure of 70 Torr and at a reflux ratio of 2. The temperature of the bottom of the distillation column was 85° C.

Consequently, a 1:0.7:0.4 (in molar ratio) mixture of ammonium acetate, acetic acid and water was recovered from the tower bottom at a rate of 66 kg/hr and an overhead of 99.0% by weight in water concentration was recovered from the tower top at a rate of 34 kg/hr.

Comparative Example D1

An aqueous ammonium acetate solution comprising ammonium acetate and water in a molar ratio of 1:4 was continuously supplied to a lower plate of a rectifying tower of 10 in theoretical plate number packed with McMahon packing at a rate of 100 kg/hr. The distilling operation was conducted at a pressure of 200 Torr and at a reflux ratio of 2. The temperature of the bottom of the distillation column was 100° C.

Consequently, a 1:0.7:0.5 (in molar ratio) mixture of ammonium acetate, acetic acid and water was recovered from the tower bottom at a rate of 51 kg/hr and a 10% by weight aqueous ammonia was recovered from the tower top at a rate of 49 kg/hr.

Comparative Example E1

Figure 2:
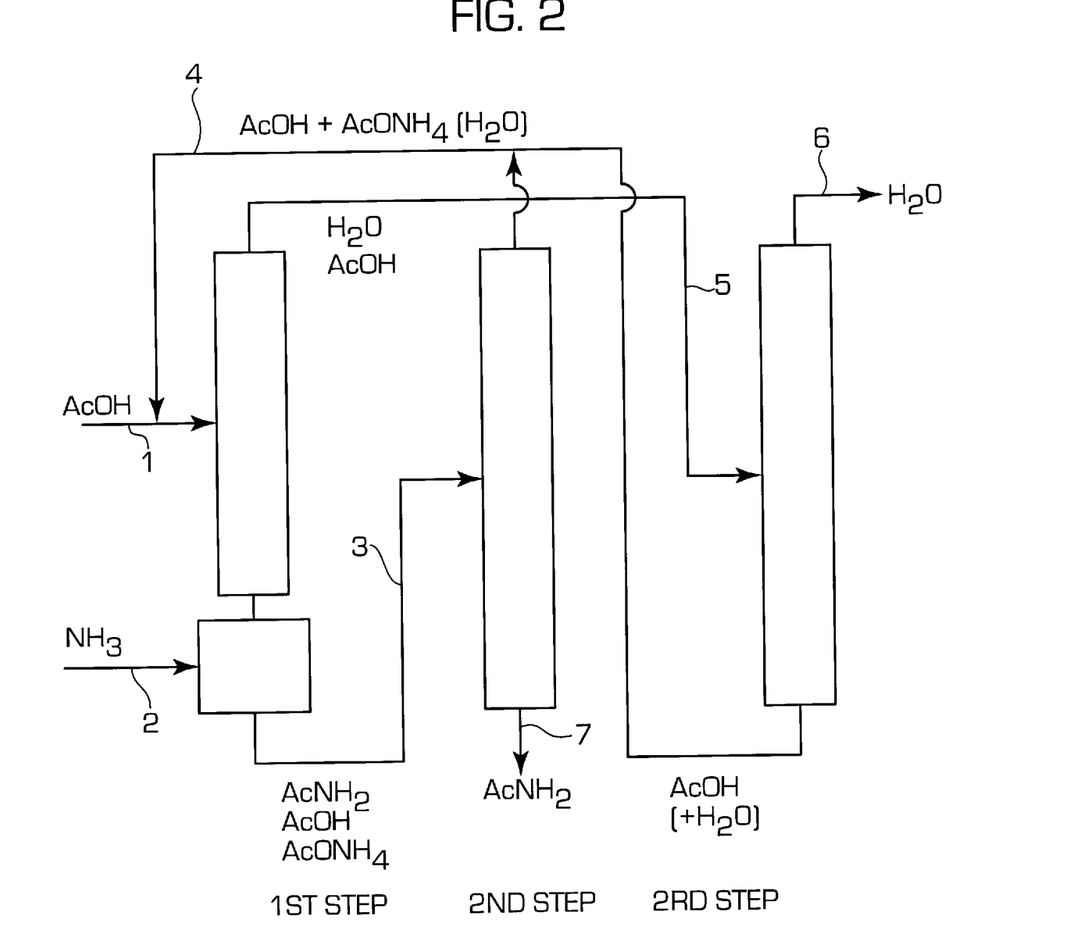
FIG. 2 is a schematic chart showing the conventional process for producing a saturated aliphatic carboxylic acid amide as described in Comparative Example E1, in which Ac is an abbreviation for a group of the formula $CH_3CO-$.

The flow of materials, products, etc. is shown by arrows in FIG. 2.
[First Step]
Acetic acid was newly continuously supplied in a rate of 114 kg/hr to a reaction vessel of 2 m³ in internal volume equipped with an agitator and also equipped with a rectifying tower of 14 in theoretical plate number packed with McMahon packing, from a lower part of the rectifying tower. Also, ammonia was continuously supplied at a rate of 32 kg/hr thereto from the reaction vessel part. The recycle acetic acid and ammonium acetate, recovered from the second and third steps, were supplied at respective rates of 72 and 8 kg/hr together with newly added acetic acid to the reaction vessel from an upper part of the rectifying tower. The operation was carried out at a reaction vessel internal temperature of 170° C., a reflux ratio of 2 and an internal capacity of 1.4 m³. A reaction fluid of 60% by weight in acetamide concentration was recovered from the reaction vessel part at a rate of 187 kg/hr, and an acetic acid/water mixture of 88% by weight in water concentration was recovered from the top of the rectifying tower at a rate of 39 kg/hr. The conversion of ammonia supplied as a raw material was 100%, the conversion of ammonium acetate was 95%, and the acetamide selectivity was 95%.
[Second Step]
The reaction fluid containing acetamide in a concentration of 60% by weight, recovered in the first step, was continuously supplied to the middle of a rectifying tower of 22 in theoretical plate number packed with McMahon packing at a rate of 187 kg/hr. The distilling operation was conducted at a pressure of 50 Torr and at a reflux ratio of 2. The distillation temperature was 143° C. Acetamide concentrate was recovered from the tower bottom at a rate of 113 kg/hr. The acetamide concentration of the concentrate was 99% by weight. A 11:1:1 (in molar ratio) mixture of acetic acid, ammonium acetate and water was recovered from the tower top at a rate of 74 kg/hr. The recovered mixture was directly fed for use as a raw material in the reaction of the first step.
[Third Step]
The acetic acid/water mixture obtained in the first step was continuously supplied to a lower plate of a rectifying tower of 50 in theoretical plate number packed with McMahon packing at a rate of 39 kg/hr. The distilling operation was conducted at a pressure of 70 Torr and at a reflux ratio of 2. The distillation temperature was 55° C.

As a result, an acetic acid/water mixture of 90% by weight in acetic acid concentration was recovered from the tower bottom at a rate of 5 kg/hr. The recovered mixture composed mainly of acetic acid was reutilized as a raw material in the reaction of the first step.

What is claimed is:

1. A process for producing a saturated aliphatic carboxylic acid amide, comprising reacting a saturated aliphatic carboxylic acid with ammonia to thereby obtain a saturated aliphatic ammonium carboxylate and subjecting the saturated aliphatic ammonium carboxylate to a dehydration reaction for obtaining a saturated aliphatic carboxylic acid amide, wherein the dehydration reaction of the saturated aliphatic ammonium carboxylate is conducted in a reaction vessel under a pressure of at least 2 kgf/cm² in a continuous manner and the amount of water present at steady state ranges from 20 to 70 mol per 100 mol of the total of the saturated aliphatic carboxylic acid, the ammonia, the saturated aliphatic ammonium carboxylate, the saturated aliphatic carboxylate acid amide, and the water.

2. The process as claimed in claim 1, which comprises:
a first step comprising:
feeding to a reaction vessel, as raw materials,
(a) the saturated aliphatic carboxylic acid, ammonia and water, and/or
(b) the saturated aliphatic ammonium carboxylate and water,
and conducting the dehydration reaction of the saturated aliphatic ammonium carboxylate in the presence of water to thereby form the saturated aliphatic carboxylic acid amide and water;
a second step comprising distilling a reaction mixture obtained in the first step containing the saturated aliphatic carboxylic acid amide and water, in a first rectifying tower so that the reaction mixture is separated into low boiling point components containing the saturated aliphatic ammonium carboxylate and water and high boiling point components containing the saturated aliphatic carboxylic acid amide, thereby obtaining the saturated aliphatic carboxylic acid amide; and a third step comprising distilling off part of water from the low boiling point components obtained in the second step in a second rectifying tower to thereby obtain an aqueous solution of saturated aliphatic ammonium carboxylate and feeding the aqueous solution to the first step.

3. The process as claimed in claim 1, wherein the dehydration reaction of the saturated aliphatic ammonium carboxylate is conducted at 130 to 250° C. under a pressure of 2 to 20 kgf/cm².

4. The process as claimed in claim 2, wherein the high boiling point components obtained in the second step, containing the saturated aliphatic carboxylic acid amide in high concentration, are further rectified to thereby separate the saturated aliphatic carboxylic acid amide from the high boiling point components to obtain a residue and wherein water is added to the residue to thereby hydrolyze side reaction products contained in the residue so that a mixture containing the saturated aliphatic carboxylic acid amide and the saturated aliphatic ammonium carboxylate is obtained, said mixture recycled to the first step or the second step.

5. The process as claimed in claim 2, wherein an alcohol of the formula: $R^2OH$ (wherein $R^2$ represents an alkyl group having 1 to 4 carbon atoms) is added to the high boiling point components obtained in the second step, containing the saturated aliphatic carboxylic acid amide in high concentration, to thereby carry out an alcoholysis of by-products contained in the high boiling point components, so that the saturated aliphatic carboxylic acid amide is obtained.

6. The process as claimed in claim 2, wherein an alcohol of the formula: $R^2OH$ (wherein $R^2$ represents an alkyl group having 1 to 4 carbon atoms) is added to a distillate obtained by further rectifying the high boiling point components obtained in the second step, containing the saturated aliphatic carboxylic acid amide in high concentration, so as to separate the saturated aliphatic carboxylic acid amide, thereby carrying out an alcoholysis of by-products contained in the distillate with the result that the saturated aliphatic carboxylic acid amide is obtained.

7. The process as claimed in claim 5, wherein the alcohol is methanol and the by-product is a saturated aliphatic dicarboxylic acid amide.

8. The process as claimed in claim 6, wherein the alcohol is methanol and the by-product is a saturated aliphatic dicarboxylic acid amide.

9. The process as claimed in claim 2, wherein, in the third step, a saturated aliphatic carboxylic acid is added to the low boiling point components obtained in the second step, containing the saturated aliphatic ammonium carboxylate and water, and distilled in the presence of 0.1 to 10 mol of the saturated aliphatic carboxylic acid per mol of the saturated aliphatic ammonium carboxylate to thereby separate water.

10. The process as claimed in any of claim 1 to 9, wherein the saturated aliphatic carboxylic acid is represented by the formula: $R^1COOH$ (wherein $R^1$ represents an alkyl group having 1 to 4 carbon atoms), the saturated aliphatic ammonium carboxylate is represented by the formula: $R^1COONH_4$ (wherein $R^1$ represents an alkyl group having 1 to 4 carbon atoms) and the saturated aliphatic carboxylic acid amide is represented by the formula: $R^1CONH_2$ (wherein $R^1$ represents an alkyl group having 1 to 4 carbon atoms).

11. The process as claimed in claim 10, wherein the saturated aliphatic carboxylic acid is acetic acid, the saturated aliphatic ammonium carboxylate is ammonium acetate and the saturated aliphatic carboxylic acid amide is acetamide.

* * * * *